United States Patent [19]

Brownell et al.

[11] 4,455,446

[45] Jun. 19, 1984

[54] METHOD OF REMOVAL OF COS FROM PROPYLENE

[75] Inventors: George L. Brownell, Monroeville Borough, Pa.; Melba Collier, Houston; William E. Hall, LaPorte, both of Tex.; Howard H. Morgan, Jr., Monroeville Borough; Arthur R. Snyder, Export Borough, both of Pa.

[73] Assignee: United States Steel Corporation, Pittsburgh, Pa.

[21] Appl. No.: 298,702

[22] Filed: Sep. 1, 1981

[51] Int. Cl.$^3$ .................. C07C 7/148; B01D 53/36
[52] U.S. Cl. .................................... 585/850; 585/851; 585/856; 208/244; 210/749; 423/244
[58] Field of Search ............ 423/244 R; 208/244; 210/749, 750; 585/850, 851, 852, 856

[56] References Cited

U.S. PATENT DOCUMENTS

| | | | |
|---|---|---|---|
| 3,050,571 | 8/1962 | Fleming et al. | 423/244 |
| 3,265,757 | 8/1966 | Frevel et al. | 585/852 |
| 4,332,781 | 6/1982 | Lieder et al. | 423/244 X |

OTHER PUBLICATIONS

Chemical Abstracts, vol. 89, 1978, p. 325, abstract 11448r.

Primary Examiner—Earl C. Thomas
Attorney, Agent, or Firm—W. Gary Goodson

[57] ABSTRACT

Carbonyl sulfide is removed from propylene by hydrolysis over a catalyst comprising platinum sulfide on alumina. Specifically, the propylene is passed through, successively, a $C_3$-splitter, a heater, the platinum sulfide catalyst bed, and a topping still where the resulting $H_2S$ and $CO_2$ are separated from the purified propylene.

9 Claims, 1 Drawing Figure

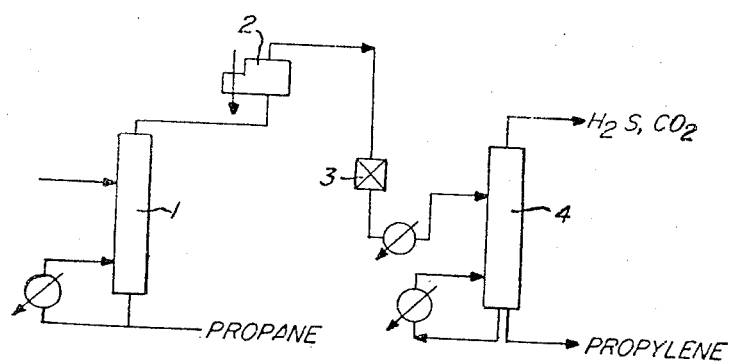

METHOD OF REMOVAL OF COS FROM PROPYLENE

BACKGROUND OF THE INVENTION

Prior to the present invention, the advent of increasingly efficient and sensitive catalysts for the polymerization of propylene has caused the polypropylene industry to recognize the importance of the control of various trace impurities in the propylene feedstock. Carbonyl sulfide has been found to be one of the most troublesome impurities, causing catalyst carryover, increased ash content of product, the production of undesirable large quantities of actactic by-product, and gross inefficiencies in catalyst life and conversion rates. These difficulties tend to be more pronounced and important in proportion to the increase in yield or efficiency otherwise observed in new catalysts.

COS levels in some polypropylene feedstocks may range from an acceptable level of $\leq 50$ ppb (parts per billion by weight) to totally unacceptable levels of over 2 ppm (parts per million by weight). In the past, a solid NaOH bed has been used commercially but NaOH alone is not capable commercially of lowering the COS concentration to $\leq 50$ ppb.

Concentrations of COS in the range of a few parts per million (e.g., 1–10 ppm) are very difficult to separate from $C_3H_6$ by fractional distillation because the boiling point of COS differs from $C_3H_6$ by only 3.4° C. Also, COS is not completely removed from propylene by the usual sulfur-removal processes such as caustic scrubbing or amine-type scrubbing due primarily to the slow rate of hydrolysis of COS.

While it is known to hydrolyze COS over a platinum sulfide/alumina catalyst, such catalysts have not been used for the hydrolysis of small amounts of COS in propylene, possibly because of the fear of deposition of polymer on the surface of the catalyst, and the difficulty of regenerating the catalyst if such a deposition occurs.

SUMMARY OF THE INVENTION

We have found that a catalyst of platinum sulfide on alumina may be used to hydrolyze very small amounts of COS in propylene in both the liquid and gas phases provided that certain conditions are maintained. The catalyst can be regenerated to remove depositions of polymerized propylene.

We are able to treat propylene containing as much as 500 or more parts per million of COS to make it acceptable for use in a highly efficient ("high yield") polymerization process, i.e. to reduce the COS content to below 50 parts per billion, by passing it through a catalyst bed of platinum sulfide on alumina. For such treatment to be practical and successful, there should be present in the propylene and/or the catalyst bed a small amount of moisture, i.e. an amount of water at least double the stoichiometric amount of the COS to be hydrolyzed. The pressure may be maintained from atmospheric to about 675 psia for the liquid phase (for the vapor phase, from atmospheric to a practical limit of about 1200 psia) and the temperature for the vapor phase should be about 250° F. to 500° F. at the inlet to the catalyst vessel, although for the liquid phase the temperature can be significantly lower, i.e. 35° C. to 65° C. The flow rate of the gas will be, preferably, 1000 to 4000 SCFH (at 14.7 psia and 70° F.) of $C_3H_6$ vapor, per cubic foot of catalyst or, for liquid, preferably below 8 hr$^{-1}$.

Water may be added, usually in the form of steam, upstream of the catalyst bed.

BRIEF DESCRIPTION OF THE DRAWING

The drawing is a flow diagram of a process for removing COS from propylene by passing the propylene through a catalyst bed.

To demonstrate our invention, certain laboratory tests were performed.

Test results obtained with PtS catalyst are summarized in Table I. The commercial catalyst contained about 0.08% platinum sulfide on an alumina support. It performed well on liquid $C_3H_6$ at space velocities of 4–5 hr$^{-1}$ (40° C.). Above 6 hr$^{-1}$ (namely, at 8 hr$^{-1}$), COS "breakthrough" occurred. The gas chromatograph analysis for COS was not sensitive below 50 ppb COS.

TABLE I

Hydrolysis of COS in Liquid Propylene on PtS/Al$_2$O$_3$ Catalyst

| Day | Temp Bed, °C. | Sapce Velocity, hr$^{-1}$ | COS-out ppb |
|---|---|---|---|
| 1* | 27 | 0.41[2] | <15[3] |
| 2 | 23 | 0.35 | <15 |
| 3 | 22 | 4.3 | 708 |
| 4 | 60 | 1.5 | <15 |
| 5 | 60 | 0.54 | <15 |
| 6 | 60 | 2.2 | <15 |
| 7 | 60 | 2.7 | " |
| 8 | 60 | 2.9 | " |
| 9 | 60 | 2.8 | " |
| 10 | 60 | 3.6 | " |
| 11 | 60 | 4.7 | " |
| 12 | 60 | 2.4 | " |
| 13 | 60 | 4.2 | " |
| 14 | 60 | 4.6 | " |
| 15 | 52 | 2.0 | " |
| 16 | 54 | 5.0 | " |
| 17 | 45 | 4.5 | " |
| 18 | 41 | 5.5 | " |
| 19 | 31 | 4.6 | 460 |

Test Conditions: Pressure (inlet) 450 psig
Bed Volume 65.6 ml
Feedstock - $C_3H_6$ containing 10 ppm $H_2O$ and dosed to 8.5 ppm COS;
$H_2O$ = 10 ppm

*Run time per day of 7 to 16+ hours.

Table II represents the results of an experiment in which the temperature was maintained relatively constant over a period of time. The catalyst was the same as used for Table I.

Conditions:
Pressure—300 psig
Reactor Temperature—100° F.
2–10.5 bed volumes per hour
Liquid Feed:
COS: 10–20 ppm wt.
$H_2O$: 40 ppm wt.
$CH_3OH$: 150 ppm wt.
$C_3H_6$(liq).: Balance

TABLE II

| Time On Stream, Hrs. | Temp., °F. | Bed Volumes per Hr. | COS ppm, wt. | | H$_2$S ppm, wt. | |
|---|---|---|---|---|---|---|
| | | | In | Out | In | Out |
| 48 | 106 | 2.0 | 10.0 | 0.00 | 0.0 | 0.0 |
| 64 | 107 | 2.0 | 9.0 | 0.00 | 0.0 | 0.47 |
| 72 | 103 | 6.0 | 7.58 | 0.00 | 0.0 | 1.18 |
| 72.5 | 103 | 8.3 | 7.58 | 0.00 | 0.0 | 3.6 |
| 80 | 103 | 9.7 | 15.5 | 0.05 | 0.0 | 1.8 |
| 96 | 102 | 8.0 | 12.0 | 0.67 | 0.0 | 4.0 |
| 104 | 100 | 4.0 | 11.6 | 0.00 | 0.0 | 3.8 |

A commercial-size run was conducted in the vapor phase and successfully reduced the COS in a commercial propylene to acceptable levels.

In this run, the data for COS is in terms of parts per million by volume in and parts per billion by volume out. (See Table III). The average amounts were 2.42 ppm in and 27 ppb out, or a 98.9% removal.

TABLE III

| Day | Time Hrs. | Pressure (psig) | °F. | Flow Rate (lbs/hr) | Moisture ppm | COS Feed ppm | COS Effluent ppb |
|---|---|---|---|---|---|---|---|
| 1 | 0900 | 285 | 291 | 23,400 | 82 | 4.06 | 10 |
| 2 | 0100 | 285 | 296 | 18,600 | 8.9 | 2.91 | 10 |
| 2 | 0700 | 285 | 300 | 15,600 | 3.8 | 4.47 | 25 |
| 3 | 0730 | 285 | 312 | 10,200 | 7.0 | 2.40 | 70 |
| 4 | 1430 | 280 | 281 | 15,000 | 7.7 | 1.17 | 40 |
| 5 | 0230 | 285 | 278 | 12,600 | 8.2 | 1.01 | 20 |
| 5 | 0900 | 275 | 290 | 16,200 | 7.3 | 2.47 | 20 |
| 6 | 0100 | 285 | 289 | 13,200 | 6.0 | 1.46 | 30 |
| 6 | 0830 | 280 | 290 | 16,500 | 7.0 | 2.18 | 30 |
| 6 | 1430 | 280 | 290 | 16,200 | 8.0 | 2.18 | 30 |
| 7 | 0830 | 280 | 290 | 12,600 | 7.0 | 2.22 | 20 |
| 8 | 0230 | 285 | 288 | 13,800 | 7.5 | 2.56 | 20 |

The configuration of the system used to conduct the commercial-size run is shown in the drawing. In the drawing, it may be seen that the propylene containing the COS is passed first to a "C$_3$ splitter" (1), the function of which is to remove propane from propylene which is the principal component of the incoming stream. The material is then optionally passed through a heater (2) usually in cases where it is preferred to employ a vapor phase system. If there is not enough water in the stream, it may be injected upstream of the catalyst bed, typically in the form of steam. Then the stream goes through the catalyst bed (3), converting COS to $CO_2$ and $H_2S$. The gas mixture is then conducted to the topping still (4), the function of which is to bleed off the acid gases, usually carried in a small amount of propylene. This propylene need not be lost but can be recovered by recycling to a "cracked gas" compressor or other recycling apparatus at the front end of the plant. The acid gases may be removed (together with any excess water) conveniently in a conventional scrubber or other treatment station such as an appropriate absorbent bed (e.g. ZnO) before or after the compressors. The "C$_3$ splitter" may be a conventional multi-stage distillation column designed to separate propylene/propane mixtures to produce "chemical grade" or "polymer grade" propylene as overhead products. The topping still is or may be a conventional multi-stage distillation column for the removal of acid gases from the product propylene. The catalyst bed is preferably a simple cylindrical vessel with an inlet at the top and an outlet at the bottom.

We claim:

1. Method of removing carbonyl sulfide from propylene comprising passing the propylene containing carbonyl sulfide over a catalyst of platinum sulfide on alumina in the presence of water to hydrolyze the COS to $H_2S$ and $CO_2$.

2. Method of claim 1 conducted in the liquid phase between about 35° C. and about 65° C., and a pressure of about 200 psia to about 450 psia.

3. Method of claim 1 conducted in the vapor phase between about 135° C. and 260° C., and a pressure at least about atmospheric.

4. Method of claim 1 wherein the carbonyl sulfide is present in the propylene in concentrations from about 50 ppb to about 500 ppm.

5. Method of claim 1 wherein the water is present in an amount at least double the stoichiometric amount of carbonyl sulfide to be removed.

6. Method of claim 1 wherein at least some of the water is injected into the propylene.

7. Method of removing carbonyl sulfide from propylene comprising passing the propylene containing carbonyl sulfide over a PtS/alumina catalyst in the presence of water to hydrolyze the COS to $H_2S$ and $CO_2$, and separating the $CO_2$ and $H_2S$ from the major part of the propylene by multi-stage distillation to obtain an acid gas stream containing propylene, $CO_2$ and $H_2S$.

8. Method of claim 7 in which the acid gas stream is treated to remove acid gases.

9. Method of claim 8 wherein the propylene from the acid gas stream is recycled to the PtS/alumina catalyst bed.

* * * * *